(12) United States Patent
Bisle et al.

(10) Patent No.: US 10,018,600 B2
(45) Date of Patent: Jul. 10, 2018

(54) SYSTEM FOR NON-DESTRUCTIVE INSPECTION OF STRUCTURAL COMPONENTS

(71) Applicant: Airbus Operations GmbH, Hamburg (DE)

(72) Inventors: Wolfgang Bisle, Hamburg (DE); Dieter Scherling, Hamburg (DE); Frederic Bock, Hamburg (DE); Markus Rahammer, Stuttgart (DE); Igor Solodov, Stuttgart (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 84 days.

(21) Appl. No.: 15/089,661

(22) Filed: Apr. 4, 2016

(65) Prior Publication Data

US 2016/0299108 A1    Oct. 13, 2016

(30) Foreign Application Priority Data

Apr. 7, 2015   (EP) .................................... 15162660

(51) Int. Cl.
   *G10K 11/00*   (2006.01)
   *G01J 5/02*    (2006.01)
   (Continued)

(52) U.S. Cl.
   CPC .......... *G01N 29/2437* (2013.01); *B06B 3/00* (2013.01); *G01J 5/02* (2013.01); *G01N 25/72* (2013.01);
   (Continued)

(58) Field of Classification Search
   CPC ........ B06B 3/00; G01N 25/72; G01N 29/221; G01N 29/2487; G01N 29/2437;
   (Continued)

(56) References Cited

U.S. PATENT DOCUMENTS 3,033,157 A * 5/1962 Sawyer .................... B06B 1/04
                                            116/137 A
3,476,851 A * 11/1969 Camossi ................... F16F 7/14
                                            264/229

(Continued)

FOREIGN PATENT DOCUMENTS

GB          1309990         3/1973

OTHER PUBLICATIONS

European Search Report, dated Sep. 8, 2015, priority document.

*Primary Examiner* — J M Saint Surin
(74) *Attorney, Agent, or Firm* — Greer, Burns & Crain, Ltd.

(57) ABSTRACT

A system for non-destructive inspection of structural components comprising an ultrasonic probe having a contact face for contacting a surface of a structural component to be inspected and being adapted to emit ultrasonic energy into the structural component when the contact face abuts on a surface of the structural component, a thermal imaging camera adapted to inspect a portion of a surface of the structural component to detect region of the surface of the structural component where an increase of the temperature occurs, and a control unit connected to the ultrasonic probe and the thermal imaging camera. The contact face extends in a plane and is provided with at least two bars which are arranged in parallel and have a common separation distance from each other.

8 Claims, 5 Drawing Sheets

(51) Int. Cl.
*G01N 29/22* (2006.01)
*G01N 29/24* (2006.01)
*B06B 3/00* (2006.01)
*G01N 25/72* (2006.01)
*G01J 5/00* (2006.01)

(52) U.S. Cl.
CPC ....... G01N 29/221 (2013.01); G01N 29/2487 (2013.01); G10K 11/002 (2013.01); *G01J 2005/0077* (2013.01); *G01N 2291/028* (2013.01); *G01N 2291/0231* (2013.01); *G01N 2291/0235* (2013.01); *G01N 2291/0258* (2013.01); *G01N 2291/0425* (2013.01); *G01N 2291/0427* (2013.01); *G01N 2291/2694* (2013.01)

(58) Field of Classification Search
CPC ... G01N 2291/0231; G01N 2291/0258; G01N 2291/0425; G01N 2291/0427; G01N 2291/2694; G01N 2291/0235; G01N 2291/028; G10K 11/002; G01J 5/02; G01J 2005/0077
USPC .......................................................... 73/632
See application file for complete search history.

(56) References Cited

U.S. PATENT DOCUMENTS

| | | | |
|---|---|---|---|
| 4,767,492 A | 8/1988 | Fukusima et al. | |
| 6,399,948 B1 | 6/2002 | Thomas et al. | |
| 6,593,574 B2 | 7/2003 | Thomas et al. | |
| 6,795,784 B1 | 9/2004 | Shepard | |
| 6,877,894 B2* | 4/2005 | Vona .................. | G01N 25/72 374/117 |
| 8,801,882 B2* | 8/2014 | Regenberg .......... | B23K 20/106 156/580.2 |
| 8,840,005 B2* | 9/2014 | Lang .................. | B23K 20/10 156/580.2 |
| 9,034,129 B2* | 5/2015 | Koetting ............. | B23K 20/10 156/64 |
| 2003/0010124 A1* | 1/2003 | Bates .................. | G01N 25/72 73/606 |
| 2004/0056200 A1* | 3/2004 | Rothenfusser ...... | G01N 25/72 250/341.1 |
| 2005/0151083 A1 | 7/2005 | Favro et al. | |
| 2010/0140325 A1 | 6/2010 | Tokutomi et al. | |

\* cited by examiner

SYSTEM FOR NON-DESTRUCTIVE INSPECTION OF STRUCTURAL COMPONENTS

CROSS-REFERENCES TO RELATED APPLICATIONS

This application claims the benefit of the European patent application No. 15162660.3 filed on Apr. 7, 2015, the entire disclosures of which are incorporated herein by way of reference.

BACKGROUND OF THE INVENTION

The present invention relates to a system for non-destructive inspection of structural components.

Non-destructive inspection of the sub-surface region of structural components is particularly important in the industrial sector, e.g., in the aviation industry where especially aircraft outer skin components need to be inspected to monitor their structural integrity. For example, after an accidental damage of an aircraft due to an outside impact, such as a stroke of lightning or a bird strike, it is important to examine the state of the sub-surface region in the respective skin element of the fuselage or wing.

Thus, inspection methods have been developed to inspect sub-surface defects in structural components without inducing damage in the components, and these methods are usually based on a combined use of ultrasonic and thermal monitoring devices.

The basic principle of the combination of ultrasonic and thermal techniques for non-destructive inspection is described in U.S. Pat. No. 6,399,948 and involves an ultrasonic probe that is coupled to a surface of a structural component to be inspected and introduces sound signals into the structural component. These sound signals propagate in an isotropic manner in all directions within the structural component. In case of a defect inside the component, the sound waves are damped through friction in the defect region. This friction results in a generation of heat at the location of the defect, i.e., a conversion of ultrasonic energy into thermal energy takes place at the position of the defect. The resulting thermal radiation can be detected with a sequence of thermal images generated with a thermal imaging camera from outside thus indicating the location of the sub-surface defect within the structural component.

U.S. Pat. No. 6,593,574 describes a similar device for the detection of sub-surface defects in a structural component by means of thermal imaging of the component while ultrasonically waves are excited in the component. This device also includes a hand-held sound "excitation gun" which comprises elongated legs for stabilizing its position and a thermal imaging camera. The sound excitation and the thermal imaging camera are controlled by a control unit for timing purposes.

U.S. Pat. No. 6,795,784 B1 further discloses a method for a non-destructive inspection of the sub-surface region of a component employing an imaging technique during which a superposition of an infrared image of the defect onto a live image of the structural component is used.

However, the prior art is characterized by a high initial energy input into the component to be inspected to effect a significant temperature increase at defects. Such a high energy input may result in damages in the component to be inspected at least at the position where the ultrasonic sound source is located. Further, a reduced energy consumption of the devices employed in the method of interest is desirable to facilitate the use of a cordless device to make the use more comfortable.

SUMMARY OF THE INVENTION

Therefore, it is an object of the present invention to provide a device with which the ultrasonic energy required for exciting a temperature increase at defects in a structural component to be inspected can be minimized.

This object is achieved by a system for non-destructive inspection of structural components, wherein the system comprises an ultrasonic probe having a contact face for contacting a surface of a structural component to be inspected and being adapted to emit ultrasonic energy into the structural component when the contact face abuts on a surface of the structural component, a thermal imaging camera adapted to inspect a portion of a surface of the structural component so as to detect a region of the surface of the structural component where an increase of the temperature occurs, and a control unit that is connected to the ultrasonic probe and the thermal imaging camera, wherein the contact face extends in a plane and is provided with at least two bars, which are arranged in parallel wherein adjacent bars have a unitary distance.

Thus, the contact face of the ultrasonic probe is provided with at least two bars extending in parallel and contacting the component to be tested. When more than two bars are used, the distance between adjacent bars is unitary for the entire arrangement.

In this way, a guided wave propagation in a predetermined direction within the structural component is achieved, i.e., along a direction perpendicular to the direction along which the parallel bars extend.

On the one hand it is conceivable that the at least two bars have a curved shape. In particular, the bars can be formed as segments of a circle having a common center. Such an arrangement results in the generation of curved planar waves which are focused to the center of the segments of a circle, so that the energy introduced by the ultrasonic probe is also focused to that point.

On the other hand the at least two bars can be formed as rectilinear bars. In this case, the point source of the ultrasonic probe transforms into a line source. The ultrasonic waves introduced in the contact area superpose constructively and propagate linearly along a distinct and parallel orientation resulting in a plane field with guided wave propagation instead of an omni-directional or isotropic field of waves.

As a consequence, the ultrasonic waves can be directed to specific regions of the component to be inspected so that the energy introduced into the component is concentrated into this region instead of stimulating all areas of the material. Thus, the overall ultrasonic energy to be introduced into the component required for exciting a temperature increase at potential defects in that specific region of the structural component can consequently be reduced compared to the case where the ultrasonic wave propagate in an isotropic manner from the position where the probe contacts the component. Therefore, a more energy efficient inspection method for structural components is made possible which method introduces less stress into the component than prior art methods.

In a preferred embodiment, the at least two bars are formed as wire filaments. Such a design of the contact face of the ultrasonic probe has the advantage that it can easily be manufactured. Further, the number and the dimensions of the wires have an influence on the amplitude of the ultrasonic waves excited inside the component to be inspected. The vibration amplitude of the ultrasonic waves increases from 16.60 mm/s to 46.89 mm/s when increasing the wire diameter from 0.3 mm to 1.1 mm. This also has a positive influence on the inspection depth within the structural component that consequently increases in the desired direction. Further, when increasing the number of the wires from two to three, regardless of the wire diameter, the amplitude of the ultrasonic waves generated in the component decreases.

The latter effect appears to occur regardless whether wires or other types of bars are employed so that it is preferred to use two bars.

In a further preferred embodiment, the at least two bars have a wedge-shaped cross section perpendicular to the longitudinal direction of the bars wherein the edge of the wedge-shaped cross section points away from the plane. Thus, when the probe abuts on a component to be inspected, the tip end of the wedge shaped cross section points towards the surface of the component and is in contact therewith which results in a particularly efficient coupling between the probe and the component.

Further, it is preferred that the unitary distance between the adjacent bars is adjustable. This adjustment is advantageous since it allows for a matching of the distance between the adjacent bars to the wavelength of a particular type of wave in the component to be inspected. In particular, different modes of Lamb waves can be excited.

In a further preferred embodiment, at least one bar comprises at least two threaded holes extending in parallel, the distance of the holes being identical for each bar, and at least two threaded rods are provided, which extend through the threaded holes and in the plane defined by the contact face. With such an adjusting device it is possible to adapt the distance between the bars by simply rotating the threaded rods. In this way, the distance between the bars can be set in a simple way in order to match the distance between the bars to a specific wavelength.

In another preferred embodiment, the ultrasonic probe comprises a sonotrode on which the contact face is provided, and a housing which receives the sonotrode and comprises an opening with a closed rim, which extends in the plane defined by the contact face, so that a closed volume inside the housing is formed when the rim abuts on a surface of a component to be inspected. Furthermore, the system preferably comprises a vacuum source, wherein the housing comprises a suction port connected with the vacuum source so that the closed volume may be evacuated. In this way the sonotrode with bars on its contact face can be fixed on the surface of a component to be inspected by applying a vacuum to the interior of the housing which abuts with its closed rim on the surface of the component to be inspected. Thus, the housing is pressed against the surface due to the pressure difference between the interior of the housing and the surroundings.

BRIEF DESCRIPTION OF THE DRAWINGS

In the following the present invention will be explained on the basis of preferred embodiments shown in the drawing, in which.

DETAILED DESCRIPTION OF THE PREFERRED EMBODIMENTS

Figure 1:
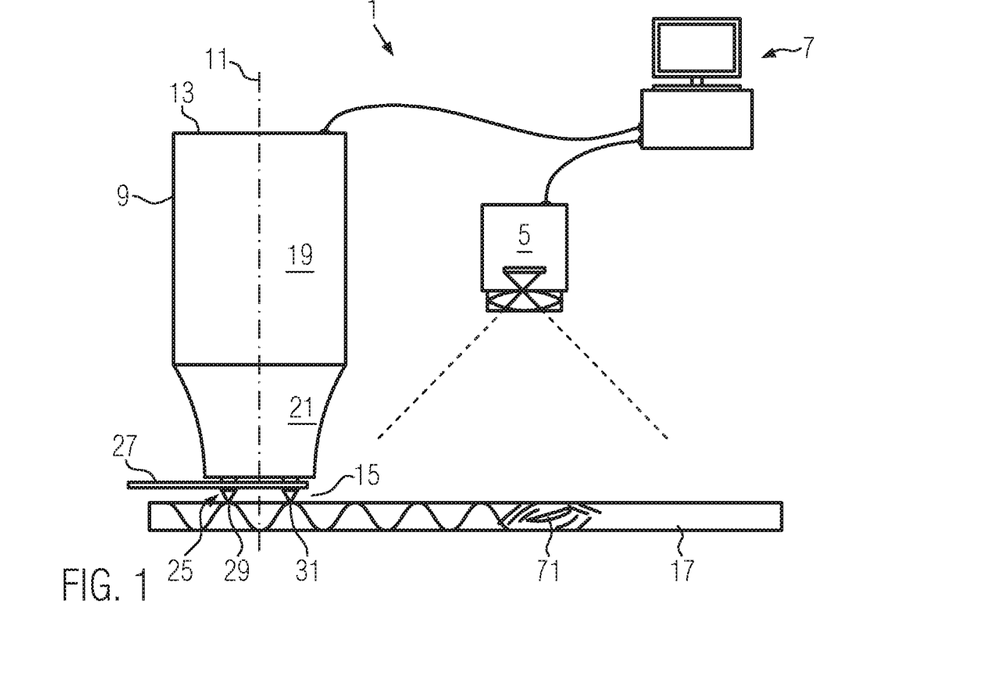
FIG. 1 shows a side view a first embodiment of a system according to the present invention.

FIG. 1 shows a first embodiment of a system 1 for non-destructive inspection of a structural component according to the present invention. The system 1 for non-destructive inspection comprises an ultrasonic probe 3, a thermal imaging camera 5 and a control unit 7.

The ultrasonic probe 3 has a substantially cylindrical casing 9 that extends along a longitudinal axis 11 having a first end surface 13 and a contact face 15, which is opposite the first end surface 13 in the direction of the longitudinal axis 11 of the ultrasonic probe 3. The surface 13 and the face 15 of the ultrasonic probe 3 are perpendicular to the longitudinal axis 11, wherein the contact face 15 is intended to contact a surface of a structural component 17 that has to be inspected. The structural component 17 is formed of a special carbon fiber reinforced plastic (CFRP) or any other material, e.g., material which can be employed to form the outer skin of an aircraft.

The ultrasonic probe 3 is adapted to emit ultrasonic energy into the structural component 17 when the contact face 15 abuts on a surface of the structural component 17. In the direction of the longitudinal axis 11, the casing 9 of the ultrasonic probe 3 comprises a piezoelectric element 19 as an ultrasonic energy source and a sonotrode 21 for the generating of ultrasonic vibrations. The contact face 15 is provided on the sonotrode 21 which has a decreasing diameter in the direction of the longitudinal axis 11 of the ultrasonic probe 3.

The thermal imaging camera 5 is adapted to screen a portion of a surface of the structural component 17 for the inspection of any sub-surface defect. The ultrasonic probe 3 and the thermal imaging camera 5 are coupled and electrically controlled with a control unit 7.

Figure 2:
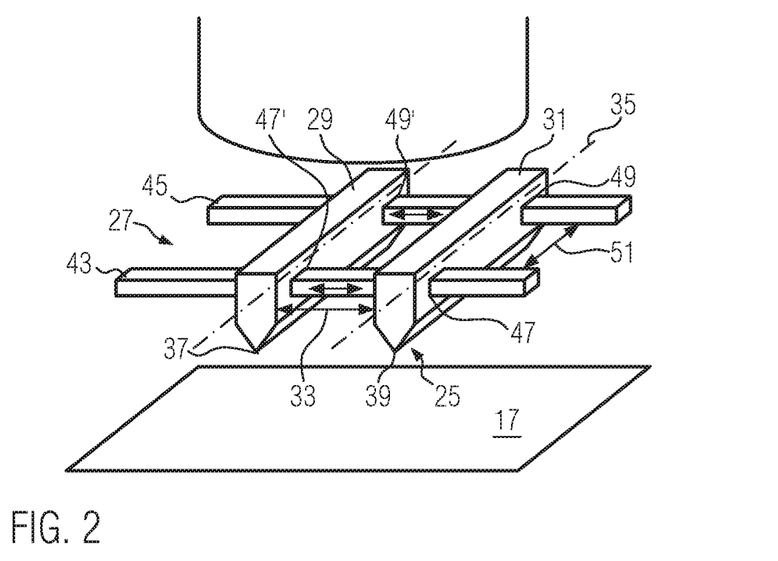
FIG. 2 shows a perspective view of the bar assembly of the system shown in FIG. 1.

A bar assembly 25 comprising at least two rectilinear bars is placed in the contact face 15 together with an adjusting device 27. FIG. 2 shows the bar assembly 25 in detail which comprises a first bar 29 and a second bar 31 which are arranged in parallel to each other and spaced by a distance 33. These rectilinear bars 29, 31 have wedge-shaped cross sections perpendicular to the longitudinal direction 35 of the bars 29, 31 wherein the narrow edges 37, 39 of the wedge-shaped cross sections point away from the plane defined by the contact 15 (see FIG. 1). These edges 37, 39 face and abut on the structural component 17 during use of the system 1 for non-destructive inspection of structural components 17.

The adjusting device 27 further comprises a first and a second threaded rod 43, 45. The first bar 29 comprises first and second threaded holes 47', 49', and the second bar 31 comprises a first and a second through hole 47, 49, which extend in parallel and perpendicular to the longitudinal direction 35 of the two bars 29, 31. Further, the distance 51 between the first and the second threaded holes 47', 49' and the through holes 47, 49 in the longitudinal direction 35 of the two bars 29, 31 is identical for each bar 29, 31, so that the threaded rods 43, 45 can extend through the through holes 47, 49 and can be threaded into the threaded holes 47', 49' of the first bar 29. The distance 33 between the adjacent bars 29, 31 is consequently adjustable with this adjusting device 27 by rotating the threaded rods 43, 45.

Figure 3:
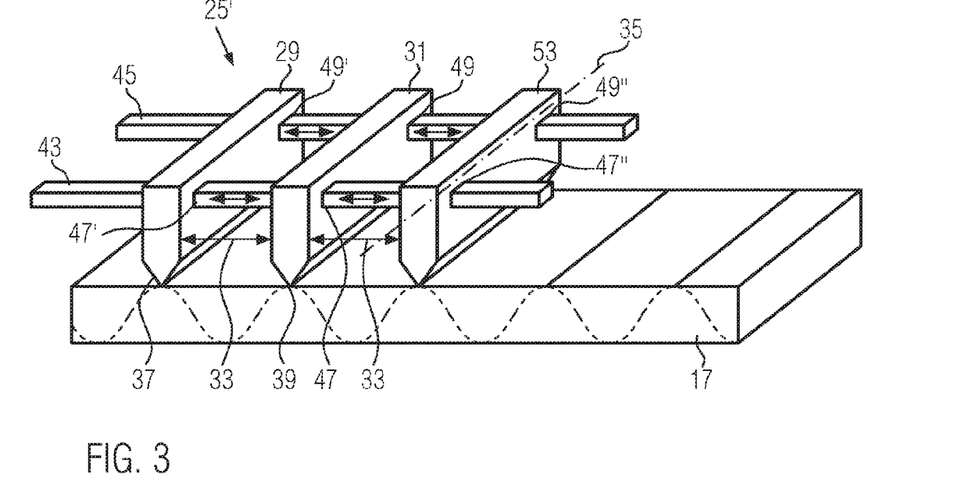
FIG. 3 shows a perspective view of an alternative of the bar assembly of the system shown in FIG. 1.

FIG. 3 depicts an alternative assembly 25' including an adjusting device 27 that differs from the first bar assembly 25 in comprising an additional third bar 53. The rectilinear third bar 53 has the same dimensions as the first and second bars 29, 31 and is arranged in parallel to the first and second bar 29, 31, wherein it also has a wedge-shaped cross section perpendicular to the longitudinal direction 35 of the bars 29, 31. The three bars 29, 31, 53 are aligned with the same unitary or common distance 33. In this case, the third bar 53 is also provided with first and second threaded holes 47", 49". However, these threaded holes 47", 49" have a left-hand thread whereas the threaded holes 47', 49' in the first bar 29 have a right-hand thread. Correspondingly, the threaded rods 43, 45 of this bar assembly 25' have right-hand threads in the region of the first bar 29 and a left-hand thread in the region of the third bar 53. Thus, rotation of the threaded rods 43, 45 results in an opposite movement of the first and third bars, 29, 53 wherein the respective distance between the respective bars 29, 31, 53 remains common, i.e., the distance between the first and the second bars 29, 31 is the same as the distance between the second bar 31 and the third bar 53.

Figure 4:
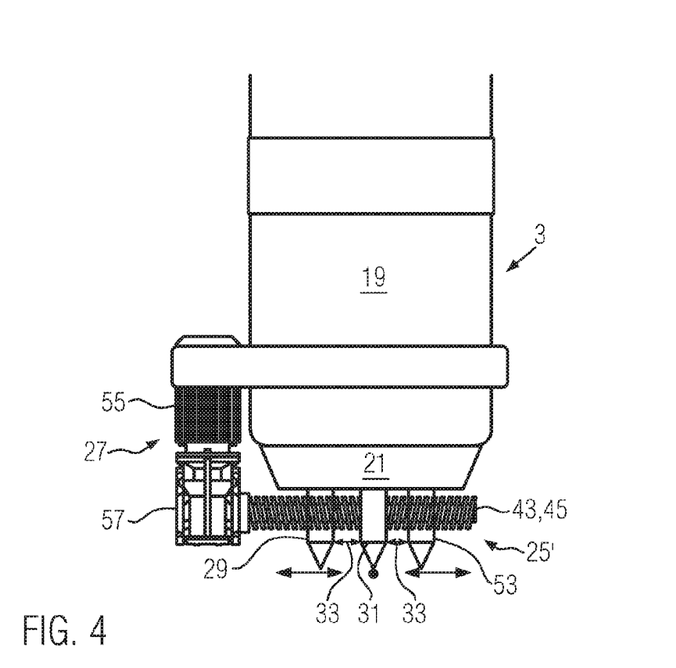
FIG. 4 shows a side view of the alternative of the bar assembly shown in FIG. 3.

In FIG. 4 the bar assembly 25' of FIG. 3 is shown mounted on the piezoelectric element 19 and the sonotrode 21. Further, in this figure it is shown that a drive motor 55 and a gearbox 57 are mounted on the combination of the piezoelectric element 19 and the sonotrode 21, wherein the output of the gearbox 57 is connected with the threaded rods 43, 45 so that the latter are rotationally driven by the drive motor 55. Since the threaded rods 43, 45 have a right-hand thread in the region of the first bar 29 and a left-hand thread in the region of the third bar 53, rotation of the threaded rods 43, 45 results either in an expansion of the distance 33 between the bars 29, 31, 53 or the distances 33 contract. The drive motor 55 is connected with the control unit 7 so that the control unit may send corresponding control signals to the drive motor 55 so as to adjust the distance 33 between the bars 29, 31, 53.

Figure 5:
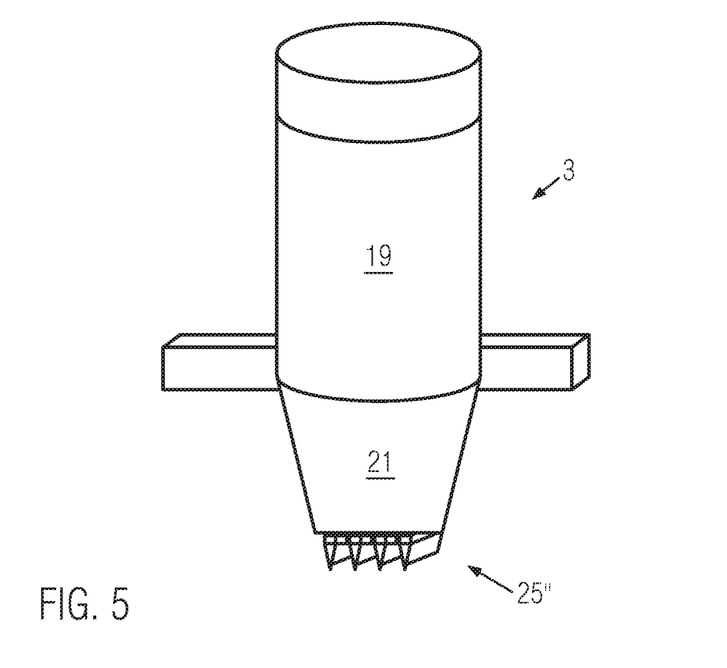
FIG. 5 shows a perspective view of the ultrasonic probe with a further alternative of a bar assembly.
Figure 6:
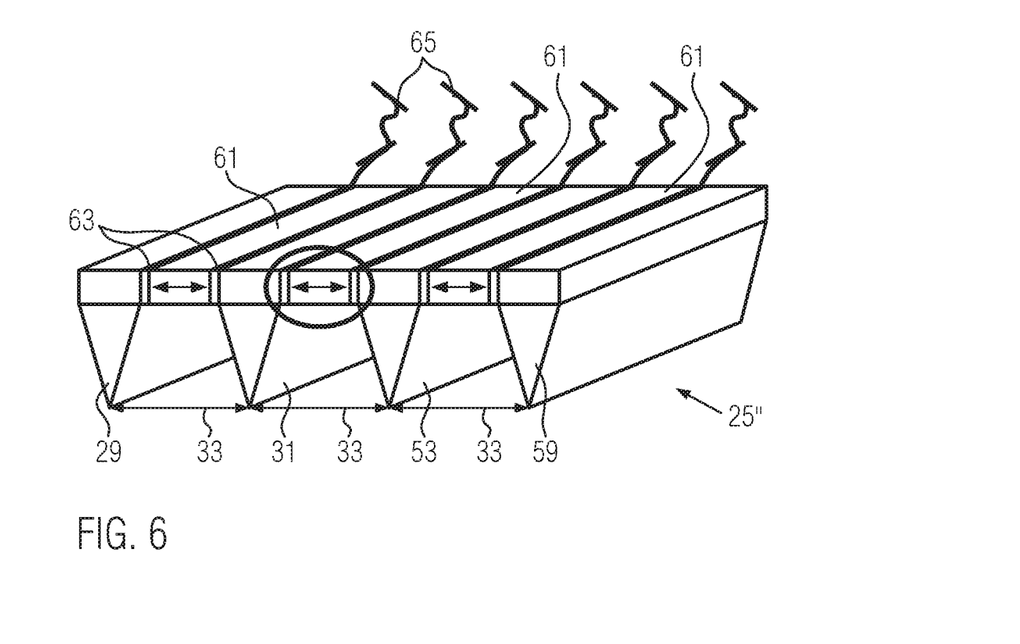
FIG. 6 shows an enlarged view of the alternative of the bar assembly of FIG. 5.

In FIGS. 5 and 6 a further alternative of a bar assembly 25" is shown. In FIG. 5 the assembly 25" is depicted mounted on the sonotrode 21 of the ultrasonic probe 3, whereas FIG. 6 shows the bar assembly 25" only. In this case, the bar assembly 25" comprises a first, a second, a third and a fourth rectilinear bar 29, 31, 53, 59 which are arranged in parallel having a unitary distance 33 between adjacent bars. As in case of the afore-mentioned bar assemblies, 25, 25', the bars 29, 31, 53, 59 have a wedge-shaped cross section perpendicular to their longitudinal distance.

Piezo elements 61 are arranged between adjacent bars 29, 31, 53, 59. These contacts 63 are connected with the control unit 7 via lines 65, so that also in this case the control unit may adjust the distance 33 between the bars 29, 31, 53, 59.

Figure 7:
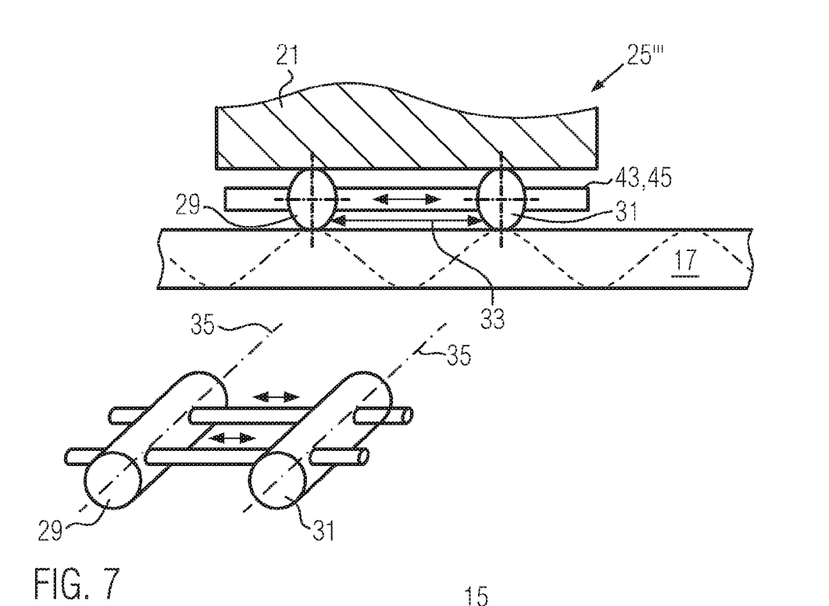
FIG. 7 shows a sectional view and a perspective view of a further alternative of the bar assembly of the ultrasonic probe of the system shown in FIG. 1.

FIG. 7 shows a further alternative bar assembly 25''' that differs from the afore-mentioned assemblies 25, 25', 25" in the shape of the cross section perpendicular to the longitudinal direction 35 of the first and the second bars 29, 31. The bars 29, 31 of the third exemplary embodiment of the adjusting device 27 are formed as wire filaments with a circular cross section perpendicular to their longitudinal direction 35. Moreover, also in this assembly 25''' threaded rods 43, 45 are employed to adjust the distance 33 between the bars 29, 31.

In further embodiments (not shown) the cross section of the bars 29, 31 may also have a rectangular, elliptic or hyperbolic shape.

Figure 8:
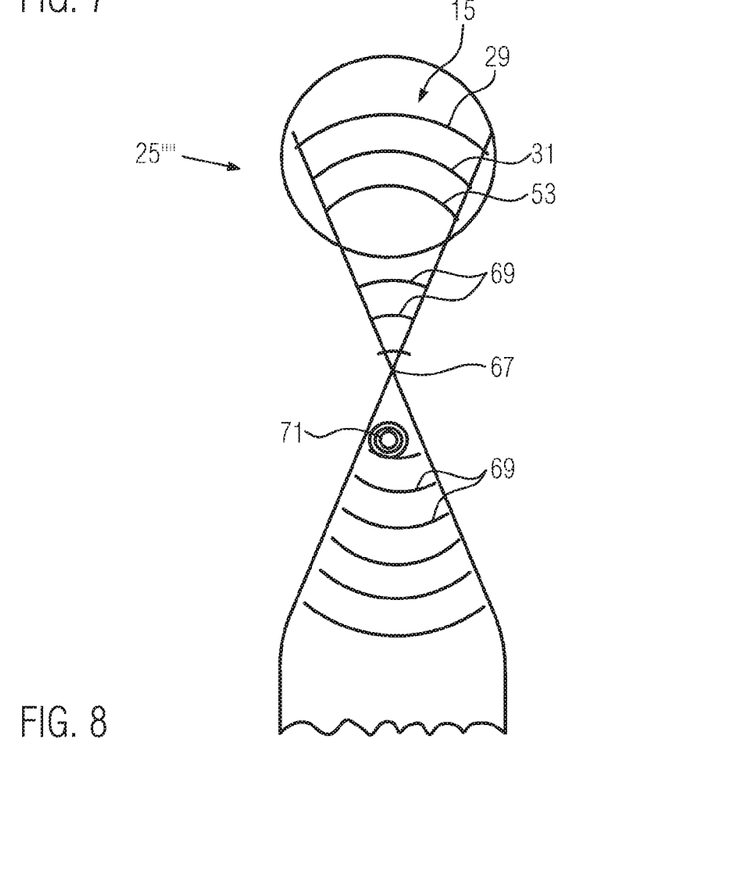
FIG. 8 shows a bottom view of a further alternative of the bar assembly of the ultrasonic probe of the system of FIG. 1.

In FIG. 8 a bottom view of a further alternative bar assembly 25'''' is shown. In this assembly 25'''' first, second and third bars 29, 31, 53 are provided, and different from the afore-mentioned assemblies the bars 29, 31, 53 have a curved shape and are arranged in parallel, i.e., the distance measure perpendicular to tangents along the bars 29, 31, 53 is unitary. In particular, the shape of the bars 29, 31, 53 is such that they are segments of a circle having a common center 67. In such an arrangement, when the ultrasonic probe 3 is activated the generated waves 69 are focused into the center 67, so that a large portion of the energy introduced by the ultrasonic probe 3 is transferred to this point. If a defect 71 is located near the center 67 of the segments of a circle describing the shape of the bars 29, 31, 53, heat will be generated in a very efficient manner in the region of this defect 71.

Figure 9:
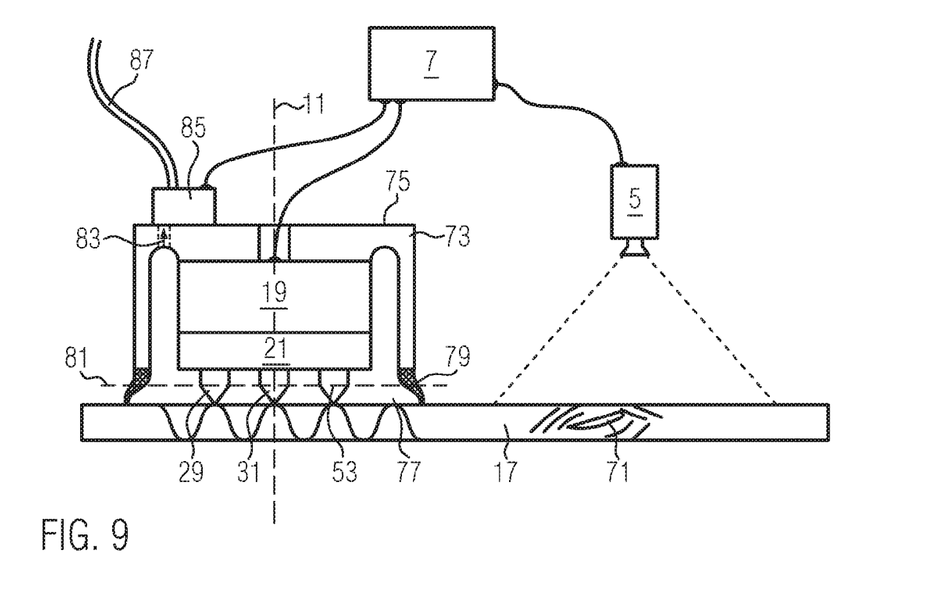
FIG. 9 shows a schematic sectional view of a second embodiment of a system for non-destructive inspection of structural components according to the present invention.

FIG. 9 shows a second embodiment of a system 1 for non-destructive inspection of structural components 17. In this embodiment, the ultrasonic probe 3 comprises a housing 73 in which the piezoelectric element 19 and the sonotrode 21 together with the bar assembly 25' and the adjusting device 27 are received. The bar assembly 25' is identical to the assembly shown in FIG. 3 and comprises three wedge-shaped bars 29, 31, 53. The housing 73 has a cylindrical cross section with a closed top end 75 and a bottom opening 77 opposite the top end 75 with respect to the longitudinal axis 11. The bottom opening 77 is surrounded by an annular closed rim 79 formed of elastic rubber material, the rim 79 extending in the plane 81 of the contact face 15 and being adapted to abut on a surface of a component 17 to be inspected. When this is the case, the housing 73 and the component 17 delimit a closed volume in which the sonotrode 21 is received.

The top end 75 of the housing 73 supports the piezoelectric element 19 and the sonotrode 21 of the ultrasonic probe 3. Further, the top end 75 is provided with a suction port 83, which is connected with a vacuum source 85. In this embodiment the vacuum source 85 employs a venture nozzle so that the vacuum nozzle is supplied with compressed air via a conduit 87.

However, it is also conceivable that the housing 73 is fixed on a flat surface of the component 17 to be inspected in a manner similar to a cup suction assembly as it is used in glass holders so that no supply of compressed air is required.

Thus, the ultrasonic probe 3 can be fixed to the surface of a component 17 to be inspected by evacuating the closed inner volume of the housing 55 by means of the vacuum source 67 or other means.

The above described embodiments of a system 1 for non-destructive inspection of structural components according to the invention operate as follows.

At the beginning, the distance 33 between the at least two bars 29, 31, 53, 59 of the respective bar assembly 25, 25', 25", 25''', 25'''' is adjusted to agree with the wavelength of the ultrasonic waves 69 to be generated within the structural component 17. This is achieved with the method depicted by the flow chart of FIG. 10.

Figure 10:
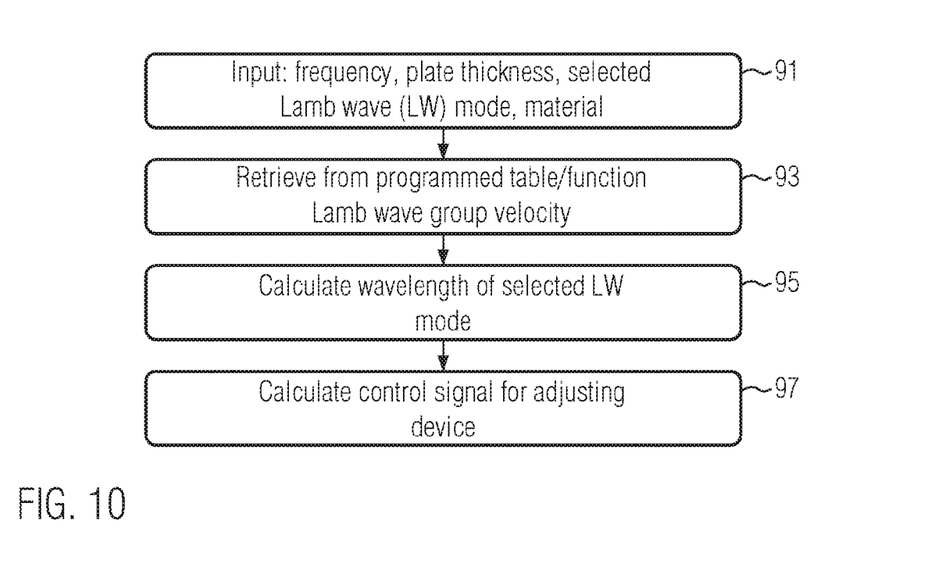
FIG. 10 shows a flow chart of the operation method for the embodiments of a system according to the present invention.

Firstly, the frequency with which the sonotrode 21 and hence the bars 29, 31, 53, 59 vibrate, the thickness of the component 17 to be inspected, the selected Lamb Wave Mode to be excited and properties such as the sound velocity are input into the control unit 7 (first step 91).

In the second step 93 the resulting Lamb Wave group velocity is retrieved from a table or function stored in the control unit 7. Based on this velocity the control unit 7 calculates in the third step 95 the wavelength of the waves 69 generated in the component 17. Finally, in a fourth step 97 the control unit 7 calculates a control signal, e.g., for the drive motor 55 or the piezo elements 61, so as to adjust the distance 33 between adjacent bars 29, 31, 53, 59 to the wavelength.

The ultrasonic probe 3 is placed onto a surface of the component 17 to inspected with the contact face 15 pointing towards the component 17, wherein in case of the second embodiment the probe 3 is fixed on the component 17 due to the vacuum generated inside the housing 73.

When the ultrasonic probe 3 is pressed against the surface of the component 17, the bars 29, 31, 53, 59 abut thereon, and when the piezoelectric element 19 is operated with the correct frequency, ultrasonic waves 69 are generated within the component 17, wherein these waves 69 propagate along a direction perpendicular to the longitudinal direction 35 of the bars 29, 31, 53. Thus, by choosing the angular position of the longitudinal direction 35 of the bars 29, 31, 53, the direction can be adjusted along which the waves 69 are focused. When there are any defects 71 in those regions which are intersected by the direction of the waves 69, heat will be generated which will be detected by the thermal imaging camera 5.

In case of the fifth alternative of a bar assembly 25'''', the waves 69 are focused into a spot, namely the center 67 of segments of a circle along which the bars 29, 31, 53 extend, and if a defect is located in the region of this center 67, it will be excited so that heat is effectively generated.

Thus, with the system according to the present invention the energy introduced by the ultrasonic probe 3 is focused along a predetermined direction or into a spot and not distributed in an isotropic manner which in turn reduces the energy which needs to be introduced when a component is to be inspected along a certain direction. This reduces the overall stress induced in the component during inspection at the point where the ultrasonic probe 3 is fixed on the component 17.

With the above described embodiments a point source of the ultrasonic energy generated by the ultrasonic probe 3 is transformed into a line source due to the at least two parallel bars 29, 31, 53, 59 in the plane of the contact face 15. This reduces the total ultrasonic energy which has to be introduced to inspect a component along a given direction.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

The invention claimed is:

1. A system for non-destructive inspection of structural components comprising:
    an ultrasonic probe having a contact face configured to contact a surface of a structural component to be inspected and being adapted to emit ultrasonic energy in the form of ultrasonic waves into the structural component when the contact face abuts on a surface of the structural component,
    a thermal imaging camera configured to inspect a portion of a surface of the structural component to detect a region of the surface of the structural component where an increase of the temperature occurs, and
    a control unit connected to the ultrasonic probe and the thermal imaging camera,
    wherein the contact face extends in a plane and is provided with at least two bars, which bars are arranged in parallel and wherein adjacent bars of the at least two bars have a common distance therebetween,
    wherein the common distance between adjacent bars of the at least two bars is adjustable for matching the common distance between adjacent bars of the at least two bars to a wavelength of the ultrasonic waves emitted by the ultrasonic probe.

2. The system according to claim 1, wherein the at least two bars are formed as rectilinear bars.

3. The system according to claim 1, wherein the at least two bars each have a curved shape.

4. The system according to claim 1, wherein the at least two bars are formed as wire filaments.

5. The system according to claim 1, wherein the at least two bars have a wedge-shaped cross section perpendicular to a longitudinal direction of the bars wherein narrow edges of the wedge-shaped cross section point away from a plane defined by the contact face.

6. The system according to claim 1, wherein at least one bar comprises at least two threaded holes extending in parallel, the distance of the threaded holes being identical for each bar having said holes, and
    wherein at least two threaded rods are provided which extend through the threaded holes and parallel to a plane defined by the contact face.

7. The system according to claim 1, wherein the ultrasonic probe comprises a sonotrode on which the contact face is provided, and
    a housing receiving the sonotrode and comprising an opening with a closed rim, which rim extends in the plane defined by the contact face, so that a closed volume inside the housing is formed when the rim abuts on a surface of a component to be inspected.

8. The system according to claim 7, further comprising a vacuum source, wherein the housing comprises a suction port connected with the vacuum source.

* * * * *